United States Patent
Sumida et al.

(10) Patent No.: US 7,122,292 B2
(45) Date of Patent: Oct. 17, 2006

(54) LACTONE COMPOUNDS, LACTONE-CONTAINING MONOMERS, THEIR POLYMERS, RESIST COMPOSITIONS USING SAME, AND PROCESSES FOR FORMING PATTERNS USING SAME

(75) Inventors: Shinichi Sumida, Saitama (JP); Haruhiko Komoriya, Saitama (JP); Katsutoshi Suzuki, Saitama (JP); Kazuhiko Maeda, Tokyo (JP)

(73) Assignee: Central Glass Company, Limited, Ube (JP)

(*) Notice: Subject to any disclaimer, the term of this patent is extended or adjusted under 35 U.S.C. 154(b) by 0 days.

(21) Appl. No.: 11/024,442

(22) Filed: Dec. 30, 2004

(65) Prior Publication Data

US 2006/0057489 A1 Mar. 16, 2006

(30) Foreign Application Priority Data

Sep. 13, 2004 (JP) ............................. 2004-266071

(51) Int. Cl.
*G03F 7/039* (2006.01)
*G03F 7/30* (2006.01)
*C07D 311/94* (2006.01)
*C08F 20/28* (2006.01)
*H01L 21/027* (2006.01)

(52) U.S. Cl. ................... 430/270.1; 430/326; 430/910; 526/281; 526/282; 549/281

(58) Field of Classification Search ................ 549/281; 430/270.1, 326, 910; 526/281, 282

See application file for complete search history.

(56) References Cited

U.S. PATENT DOCUMENTS

| 6,280,898 B1 * | 8/2001 | Hasegawa et al. ....... 430/270.1 |
| 2001/0026901 A1 * | 10/2001 | Maeda et al. ............ 430/270.1 |
| 2002/0102492 A1 * | 8/2002 | Iwai et al. ................ 430/270.1 |

FOREIGN PATENT DOCUMENTS

| JP | 2000-26446 | 1/2000 |
| JP | 2000-159758 | 6/2000 |
| JP | 2002-162745 A | 6/2002 |
| JP | 2003-002882 A | 1/2003 |
| JP | 2003-005374 A | 1/2003 |
| JP | 2003-55363 | 2/2003 |
| JP | 2003-055363 A | 2/2003 |
| JP | 2004-175981 A | 6/2004 |

OTHER PUBLICATIONS

JP patent office English translation of JP 2003055363, Feb. 26, 2003, cited on applicant's IDS.*
Davies, David I. et al., "Contrasting Reactions of Silver Perchlorated and Silver Tosylate with 6-endo-hydroxy-5-exo-lodonorborn-2-endo-ylacetic acid ∂-lactone", Chemistry & Industry, (1981), (19), pp. 693-694.
International Search Report dated Dec. 6, 2005 with an English translation of the pertinent portion (five (5) pages).

* cited by examiner

*Primary Examiner*—Richard L. Schilling
(74) *Attorney, Agent, or Firm*—Crowell & Moring LLP

(57) ABSTRACT

The present invention relates to novel first to fourth lactone compounds. The first lactone compound is represented by the formula (1),

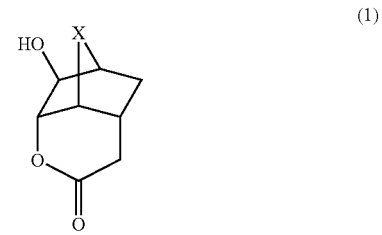

(1)

in the formula, X represents $CH_2$, $CH_2CH_2$, O, S or $NR^1$, and $R^1$ represents hydrogen atom, a straight-chain, branched or cyclic alkyl group of a carbon number of 1–10. Hydrogen(s) of the alkyl group may partially or entirely be replaced with fluorine atom(s). Furthermore, a part of the alkyl group may contain an atomic group containing oxygen atom, sulfur atom, nitrogen atom, carbon-carbon double bond, carbonyl group, hydroxy group or carboxyl group.

8 Claims, No Drawings

LACTONE COMPOUNDS, LACTONE-CONTAINING MONOMERS, THEIR POLYMERS, RESIST COMPOSITIONS USING SAME, AND PROCESSES FOR FORMING PATTERNS USING SAME

BACKGROUND OF THE INVENTION

The present invention relates to (1) a compound having a six-membered ring lactone and a norbornane ring in the same molecule and its monomer, (2) a high-molecular compound containing the monomer as a constituent unit, (3) a resist material containing this high-molecular compound, and (4) a pattern forming method using this resist material.

In recent years, as operation data to deal with and the amount of processing two-dimensional and three-dimensional image data have become enormous by the development of computers and digital equipment represented by electric home appliances, high-capacity and high-speed semiconductor devices are necessary. Along with the development of network such as Internet, the processing capacity required for digital equipment is becoming higher.

In order to achieve this requirement, higher density and higher integration of semiconductor devices, that is, finer pattern rule is required. As one of means for achieving finer ones, it is known to shorten the wavelength of an exposure light source used when resist pattern is formed. Hitherto, i-line (365 nm) of high-pressure mercury light and KrF excimer laser light (248 nm) have been used as the exposure light source. Now, 0.13 µm or less is required as the minimum line width. Since i-line and KrF excimer laser light used hitherto cannot respond to the processing for that, the use of ArF excimer laser (193 nm) has begun. The development of photolithography technique using $F_2$ (157 nm) and EUV extreme ultraviolet rays is in progress for the purpose of processing finer patterns.

In ArF excimer laser lithography, since resins such as novolac and polyvinylphenols (aromatics) used for KrF excimer laser have a strong absorption at around 193 nm, they cannot be used as base resins for ArF resist. Therefore, acrylic resins, which are replacement of aromatic by aliphatic for improving transparency, are mainly studied. As to $F_2$ laser lithography, finer ones of 0.10 µm or less is expected, and it is found that fluorine-containing polymers are effective for securing transparency.

The base resin is required to have capacities such as acid lability, etching resistance and substrate adhesion as well as transparency to laser light. Since there is no monomer having all the capacities, it is tried to satisfy the required characteristics by using a copolymer formed from a plurality of monomers having respective capacities. However, high molecular compounds capable of practical use have not yet been obtained. Thus, the development of various monomers that sufficiently demonstrate respective capacities is now actively going on.

Above all, the development of a monomer having substrate adhesion has been difficult. This is because, since substrate adhesion has been achieved up to now by hydroxy group and carboxy group, which are hydrophilic groups, and in contrast etching resistance has been provided by polycyclic hydrocarbon groups such as adamantyl and norbornyl, the by-production of homopolymers, the formation of block copolymers and the like have occurred frequently, and therefore it has been difficult to make the reaction proceed homogeneously. It has been found that resist resolution lowers extremely by using a high molecular compound obtained under such condition as a base resin of resist material. That is because there occur swelling caused by penetration of a developing solution into a hydrophilic moiety arranged biasedly, pattern collapse caused by exfoliation of a highly hydrophobic moiety, inhomogeneous dissolution caused by resist film inner layer separation, and the like.

In order to solve the above problems, a tricyclic lactone having a five-membered ring lactone structure and a norbornane ring has recently been developed (see Japanese Patent Laid-open Publication No. 2000-26446 and Japanese Patent Laid-open Publication No. 2000-159758). Since this has in the same molecule a five-membered ring lactone structure as a hydrophilic group for providing substrate adhesion and a norbornane ring as a hydrophobic group, the separation of the hydrophilic moiety and the hydrophobic moiety cannot occur in principle. As a result, it was confirmed that a homogeneous high molecular compound having a good dissolution characteristic is obtained and that stiffness of the condensed tricyclic moiety provides the high molecular compound with a sufficient etching resistance. However, it was found that, since the five-membered ring lactone is stiff beyond expectation, all of the unshared electron pairs of the oxygen atoms of the lactone moiety cannot contribute to substrate adhesion, and it is inferior to the expected capability and is still insufficient for practical level. Furthermore, the polymerization solvent is limited since its dissolution in organic solvent is low. It was very difficult to remove the monomer upon purification of the high molecular compound. Therefore, creation of a novel lactone-containing monomer or its raw material, which can overcome those defects, was strongly desired.

SUMMARY OF THE INVENTION

The present invention was made in view of the above situation, and its object is to provide (1) a novel tricyclic lactone compound having a six-membered ring lactone compound and a norbornane ring, which are built therein, and its monomer, (2) a high molecular compound derived from the monomer, (3) a resist material in which the high molecular compound is used as a base resin, and (4) a pattern forming process using the resist material.

According to the present invention, a first lactone compound represented by the formula (1) is provided.

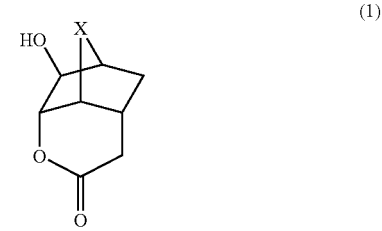

(1)

In the formula, X represents $CH_2$, $CH_2CH_2$, O, S or $NR^1$, and $R^1$ represents hydrogen atom, a straight-chain, branched or cyclic alkyl group of a carbon number of 1–10. Hydrogen(s) of the alkyl group may partially or entirely be replaced with fluorine atom(s). Furthermore, a part of the alkyl group may contain an atomic group containing oxygen atom, sulfur atom, nitrogen atom, carbon-carbon double bond, carbonyl group, hydroxy group or carboxyl group.

According to the present invention, the first lactone compound may be a second lactone compound represented by the formula (2).

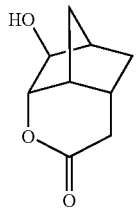

(2)

According to the present invention, a lactone-containing monomer (a third lactone compound) represented by the formula (3) is provided.

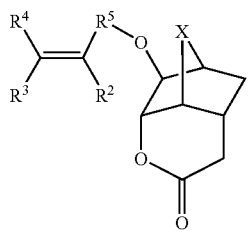

(3)

In the formula, X represents $CH_2$, $CH_2CH_2$, O, S or $NR^1$.

Each of $R^1$ to $R^4$ independently represents hydrogen atom, halogen atom, or a straight-chain, branched or cyclic alkyl group of carbon number of 1–10. Hydrogen(s) of the alkyl group may partially or entirely be replaced with fluorine atom(s). Furthermore, a part of the alkyl group may contain an atomic group containing oxygen atom, sulfur atom, nitrogen atom, carbon-carbon double bond, carbonyl group, hydroxy group or carboxyl group.

$R^5$ represents a single bond, $CH_2$ or carbonyl group.

According to the present invention, a lactone-containing acrylate derivative (a fourth lactone compound) represented by the formula (4) is provided.

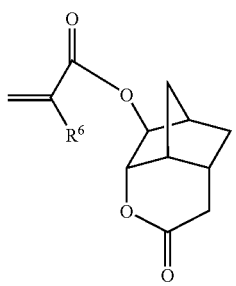

(4)

In the formula, $R^6$ represents a functional group selected from the group consisting of hydrogen atom, fluorine atom, methyl group and trifluoromethyl group.

According to the present invention, it is possible to provide a first high molecular compound by a polymerization or copolymerization using the above lactone-containing monomer or lactone-containing acrylate derivative. This high molecular compound may a second high molecular compound obtained by copolymerizing the above lactone-containing monomer or lactone-containing acrylate derivative with a monomer having acid lability.

According to the present invention, it is possible to provide a first resist material containing the first or second high molecular compound. The first resist material may be a second resist material of chemically amplified type containing the first or second high molecular compound and a photoacid generator.

According to the present invention, it is possible to provide a pattern forming process comprising the steps of:
(a) applying the first or second resist material to a substrate to form a resist film;
(b) exposing the resist film to a high energy ray of a 1–300 nm wavelength band through a photomask;
(c) heating the exposed resist film; and
(d) developing the heated resist film with a developing solution.

The high energy ray of the step (b) may be KrF laser, ArF laser, $F_2$ laser, EUV laser or X-ray.

DETAILED DESCRIPTION

As a result of the present inventors' repeated eager examinations to achieve the above object, we found a novel tricyclic lactone compound having a six-membered ring lactone structure and a norbornane ring, which are built therein, and its monomer. We confirmed that a high molecular compound prepared by a polymerization or copolymerization using this monomer has a high transparency in a wide wavelength region from ultraviolet region to near infrared region and has a sufficient etching resistance and an appropriate developing solution penetration due to the condensed tricyclic moiety and that it is superior to conventional products in substrate adhesion because almost all of the unshared electron pairs on the oxygen could have contributed to substrate adhesion because the six membered ring lactone moiety can move freely as compared with a five membered ring lactone. Furthermore, since there was an effect of dramatically increasing dissolution in organic solvent by making it one methylene chain longer than five-membered ring lactone, not only the selection of polymerization solvent has become wide, but also the removal of monomer upon purification of the high molecular compound was found to become easy. Finally, we completed the present invention by providing a resist material using the high molecular compound equipped with the above performances as a base resin and by finding a pattern forming process using the resist material.

In the present invention, it was found that resist material improves in transparency, substrate adhesion, developing solution penetration and etching resistance by using a high molecular compound prepared by a polymerization or copolymerization using a monomer represented by the formula (3) or (4) having a six membered ring lactone structure and a norbornane ring, which are built therein, as a base resin of resist material. Therefore, the resist material of the present invention provides a resist material having a high transparency in a wide wavelength region from ultraviolet region to near infrared region, a high adhesion to substrate, an appropriate developing solution penetration, and a high etching resistance. Furthermore, it is possible to easily form patterns that are fine and perpendicular to substrate by the pattern forming process of the present invention. The resist material of the present invention is suitable as a fine pattern forming material for producing VLSI.

In the following, the present invention is explained in detail. Hitherto, substrate adhesion has been demonstrated by hydroxy group and carboxyl group, which are hydrophilic groups, and by-production of homopolymers and the generation of block copolymers have occurred frequently in polymerizations with hydrophobic monomers having polycyclic hydrocarbon groups such as adamantyl group. As a result, there occur pattern collapse caused by exfoliation of a highly hydrophobic moiety, swelling caused by penetration of a developing solution into a hydrophilic moiety arranged biasedly, inhomogeneous dissolution caused by resist film inner layer separation, and the like. Thus, it was found that resist resolution becomes extremely low.

Recently, a tricyclic lactone having a five-membered ring lactone structure and a norbornane ring has been developed. Since substrate adhesion is demonstrated by a lactone structure of hydrophilic group, and since it also has in the same molecule a norbornane ring that is a hydrophobic group, the separation of the hydrophilic moiety and the hydrophobic moiety does not occur. As a result there was obtained a homogeneous high molecular compound having a good dissolution characteristic. However, it was found that, since the five-membered ring lactone is stiff beyond expectation, all of the unshared electron pairs of the oxygen atoms of the lactone moiety cannot contribute to substrate adhesion, and it is inferior to the expected capability and is still insufficient for practical level. Furthermore, it is known that the polymerization solvent is limited since its dissolution in organic solvent is low and that it is very difficult to remove the monomer upon purification of the obtained high molecular compound.

In contrast with this, since the monomer represented by the formula (3) or (4) has a six membered ring lactone structure, the lactone moiety can move more freely as compared with a five membered ring, almost all of the unshared electron pairs on the oxygen can contribute to substrate adhesion, and it was found to have a capability superior to conventional products. Furthermore, since there was an effect of increasing dissolution in organic solvent by making it one methylene chain longer, not only the selection of polymerization solvent has become wide, but also the removal of monomer upon purification of the high molecular compound became easy. Of course, due to having a high etching resistance and an appropriate developing solution penetration by the condensed tricyclicity similar to five membered lactone compounds, a resist material containing this high molecular compound as a base resin was found to form a pattern superior in rectangularity, not to cause exfoliation, and to be strong in etching.

Thus, the present invention provides lactone compounds represented by the formulas (1) to (4), monomers containing them, and their high molecular compounds. A resist material using this dramatically improves substrate adhesion and makes it possible to obtain a rectangular patterning, while it has high transparency, high etching resistance and appropriate developing solution penetration.

In the following, the present invention is explained in more detail. In the compounds represented by the formulas (1) to (4) of the present invention, as long as their capabilities such as substrate adhesion are not damaged, hydrogens of the compounds of the formulas (1) to (4) may be replaced with various functional groups.

In the compound represented by the formula (1) of the present invention, X represents $CH_2$, $CH_2CH_2$, O, S or $NR^1$, and $R^1$ represents hydrogen atom, a straight-chain, branched or cyclic alkyl group of a carbon number of 1–10. Hydrogen(s) of the alkyl group may partially or entirely be replaced with fluorine atom(s). Furthermore, a part of the alkyl group may contain an atomic group containing oxygen atom, sulfur atom, nitrogen atom, carbon-carbon double bond, carbonyl group, hydroxy group or carboxyl group.

The straight-chain, branched or cyclic alkyl group of a carbon number of 1–10, which is usable as $R^1$, can be exemplified by methyl group, ethyl group, propyl group, isopropyl group, cyclopropyl group, n-propyl group, sec-butyl group, tert-butyl group, cyclobutyl group, n-pentyl group, cyclopentyl group, sec-pentyl group, neopentyl group, hexyl group, cyclohexyl group, ethylhexyl group, pentenyl group, octyl group, nonanyl group, decanyl group, norbornel group, adamantyl group, vinyl group, allyl group, butenyl group, pentenyl group, ethynyl group, and the like. Those containing oxygen atom, nitrogen atom, sulfur atom, carbonyl bond, hydroxy group or carboxyl group are functional groups contained or intervene in the forms of —OH, $—OR^6$, —O—, —C(=O)—, —C(=O)O—, $—CO_2H$, $—CO_2R^6$, —S—, —S(=O)—, $—S(=O)_2—$, $—NH_2—$, $—NHR^6—$, $—N(R^6)_2—$ and the like in the above alkyl groups. $R^6$ represents a straight-chain, branched or cyclic alkyl group of a carbon number of 1–10. It is possible to use functional groups in which the alkyl groups and alkyl groups containing hetero atoms have partially or entirely been replaced with fluorine atoms.

The compound represented by the formula (2) of the present invention is preferably used as a raw material of the six membered ring lactone containing monomer of the present invention and is the most basic lactone compound for inducing various lactone containing monomers represented by the formula (3) or (4).

X of the compound represented by the formula (3) represents $CH_2$, $CH_2CH_2$, O, S or $NR^1$, and $R^1$ represents hydrogen atom, a straight-chain, branched or cyclic alkyl group of a carbon number of 1–10. Hydrogen(s) of the alkyl group may partially or entirely be replaced with fluorine atom(s). Furthermore, a part of the alkyl group may contain an atomic group containing oxygen atom, sulfur atom, nitrogen atom, carbon-carbon double bond, carbonyl group, hydroxy group or carboxyl group.

The straight-chain, branched or cyclic alkyl group of a carbon number of 1–10, which is usable as $R^1$, can be exemplified by methyl group, ethyl group, propyl group, isopropyl group, cyclopropyl group, n-propyl group, sec-butyl group, tert-butyl group, cyclobutyl group, n-pentyl group, cyclopentyl group, sec-pentyl group, neopentyl group, hexyl group, cyclohexyl group, ethylhexyl group, pentenyl group, octyl group, nonanyl group, decanyl group, norbornel group, adamantyl group, vinyl group, allyl group, butenyl group, pentenyl group, ethynyl group, and the like. Those containing oxygen atom, nitrogen atom, sulfur atom, carbonyl bond, hydroxy group or carboxyl group are functional groups contained or intervene in the forms of —OH, $—OR^6$, —O—, —C(=O)—, —C(=O)O—, $—CO_2R^6$, —S—, —S(=O)—, $—S(=O)_2—$, $—NH_2—$, $—NHR^6—$, $—N(R^6)_2—$ and the like in the above alkyl groups. $R^6$ represents a straight-chain, branched or cyclic alkyl group of a carbon number of 1–10. It is possible to use functional groups in which the alkyl groups and alkyl groups containing hetero atoms have partially or entirely been replaced with fluorine atoms.

$R^2$ to $R^4$ of the compound represented by the formula (3) represent hydrogen atoms, halogen atoms or straight-chain, branched or cyclic alkyl groups of a carbon number of 1–10. Hydrogen(s) of the alkyl group may partially or entirely be replaced with fluorine atom(s). Furthermore, a part of the alkyl group may contain an atomic group containing oxygen atom, sulfur atom, nitrogen atom, carbon-carbon double bond, carbonyl group, hydroxy group or carboxyl group. The straight-chain, branched or cyclic alkyl groups of a carbon number of 1–10, which are usable as $R^2$ to $R^4$, can be exemplified by methyl group, ethyl group, propyl group, isopropyl group, cyclopropyl group, n-propyl group, sec-butyl group, tert-butyl group, cyclobutyl group, n-pentyl group, cyclopentyl group, sec-pentyl group, neopentyl group, hexyl group, cyclohexyl group, ethylhexyl group, pentenyl group, octyl group, nonanyl group, decanyl group, norbornel group, adamantyl group, vinyl group, allyl group, butenyl group, pentenyl group, ethynyl group, and the like. Those containing oxygen atom, nitrogen atom, sulfur atom, carbonyl bond, hydroxy group or carboxyl group are functional groups contained or intervene in the forms of —OH, —OR$^6$, —O—, —C(=O)—, —C(=O)O—, —CO$_2$R$^6$, —S—, —S(=O)—, —S(=O)$_2$—, —NH$_2$—, —NHR$^6$—, —N(R$^6$)$_2$— and the like in the above alkyl groups. $R^6$ represents a straight-chain, branched or cyclic alkyl group of a carbon number of 1–10. It is possible to use functional groups in which the alkyl groups and alkyl groups containing hetero atoms have partially or entirely been replaced with fluorine atoms. $R^5$ of the compound represented by the formula (3) represents a single bond, CH$_2$, or carbonyl group.

According to the present invention, the compound represented by the formula (4) is preferably used as a base compound of a six membered ring lactone containing acrylate of the present invention. According to the present invention, the compound represented by the formula (4) (in the formula $R^6$ is one functional group of hydrogen atom, fluorine atom, methyl group and trifluoromethyl group) is the most basic compound of various six membered ring lactone containing monomers represented by the formula (3).

Next, a synthesis process of the compound represented by the formula (1) or (2) is explained.

The compound represented by the formula (1) or (2) is derived from a corresponding carboxylic acid. If it is exemplified with the formula (2), it is a process (see Japanese Patent Laid-open Publication 2003-55363) of synthesizing a six membered ring lactone compound represented by the formula (2) by reacting a carboxylic acid represented by the formula (5) with hydrogen peroxide aqueous solution.

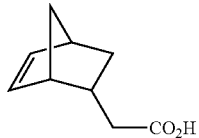

(5)

As the hydrogen peroxide aqueous solution used in the present invention, it is generally preferable to use a hydrogen peroxide aqueous solution of a concentration of about 30% in terms of economy and safety.

Although the amount of the hydrogen peroxide aqueous solution to be used is not particularly limited, it is generally preferably in a range of 1–20 equivalents in terms of hydrogen peroxide to the unsaturated carboxylic acid (the formula (5)), more preferably in a range of 1–10 equivalents from the viewpoints of operability and economy.

As an accelerator of the present reaction, hydrogencarbonate is effective. As the hydrogencarbonate, for example, there are cited hydrogencarbonates of alkali metals such as sodium and potassium, hydrogencarbonates obtained by introducing carbon dioxide into an aqueous solution of amine, and ammonium hydrogencarbonate. As such amine, there are cited primary amines such as methylamine, ethylamine, propylamine, isopropylamine, butylamine, isobutylamine, hexylamine, cyclohexylamine, octylamine, ethanolamine, 2-methoxyethylamine, 3-methoxypropylamine, and 3-ethoxypropylamine; and secondary amines such as dimethylamine, diethylamine, dibutylamine, dioctylamine, diethanolamine, pyrrolidine, piperidine, and morpholine. It is also possible to use a compound having at least two nitrogen atoms in one molecule, which is obtained by combining these amines with a suitable spacer. As such compound, for example, there are cited ethylenediamine, hexamethylenediamine, and nonanediamine. Of these, it is preferable to use the above hydrogencarbonate as hydrogencarbonate from the viewpoint of obtaining a lactone not containing metal component as impurity. It is more preferable to use ammonium hydrogencarbonate from the viewpoints of availability and economy. The method of adding hydrogencarbonate is not particularly limited. It is possible to use a method in which hydrogencarbonate itself or its solution is added into the system, a method in which carbon dioxide is introduced into the above-mentioned amine or ammonia aqueous solution to generate hydrogencarbonate in the system, and the like.

Although the amount of hydrogencarbonate to be used is not particularly limited, it is preferably in a range of 1–10 equivalents, more preferably in a range of 1–5 equivalents from the viewpoints of operability, economy and reaction rate, relative to the unsaturated carboxylic acid derivative represented by the formula (5).

In the present invention, water is used as solvent. It suffices that the amount of solvent to be used is sufficient for dissolving hydrogencarbonate. Although it depends on the kind of hydrogencarbonate to be used, a range of 5–20 parts by weight to one part by weight of hydrogencarbonate is generally preferable.

The reaction temperature is preferably in a range of 0–60° C., more preferably in a range of 20–50° C. In case that the reaction temperature exceeds 60° C., yield per hydrogen peroxide tends to lower due to self-decomposition of hydrogen peroxide. In case that it is lower than 10° C., the reaction rate becomes extremely slow, and yield tends to lower due to prolonged residence time. Both cases are not preferable.

A lactone obtained by the above method can be isolated and purified by methods generally used for isolation and purification of organic compounds. For example, an extraction is conducted by adding an organic solvent such as ethyl acetate to the reaction mixture, and the resulting organic layer is concentrated, followed by purification such as distillation, recrystallization and column chromatography.

Next, a process of synthesizing a compound represented by the formula (3) or (4) is explained.

The compound represented by the formula (3) or (4) is derived from the lactone compound represented by the formula (1) or (2). If it is exemplified with the formula (4), it is a process of synthesizing a lactone containing acrylate represented by the formula (4) by reacting the lactone compound represented by the formula (2) with an acrylic acid derivative in the presence of acid or base.

The acrylic acid derivative can be exemplified by acrylic acid, methacrylic acid, trifluoromethacrylic acid, acrylic acid anhydride, methacrylic acid anhydride, trifluoromethacrylic acid anhydride, acrylic acid chloride, methacrylic acid chloride, and trifluoromethacrylic acid chloride. It is possible to use carboxylic acid and anhydride in the presence of acid and to use acid chloride in the presence of base. Since a suitable reaction rate can be obtained in the case of using anhydride, it is preferably used. It suffices that the acrylic acid derivative is used in an amount of 1 mol or greater to 1 mol of the lactone derivative (the formula (2)) as the raw material. An amount of 1.1 to 2 times that by mol is preferable from the viewpoints of reaction rate and yield of the target lactone containing acrylate (the formula (4)).

The usable acids are protonic acids and Lewis acids. As they are exemplified, there are cited protonic acids such as hydrogen fluoride, sulfuric acid, phosphoric acid, hydrogen chloride, methanesulfonic acid, trifluoromethanesulfonic acid and trifluoroacetic acid; and Lewis acids such as aluminum chloride, aluminum bromide, gallium chloride, gallium bromide, ferric chloride (FeCl3), zinc chloride, antimony chloride, titanium tetrachloride, tin tetrachloride, boron trifluoride, $Ti(OCH_3)_4$, $Ti(OC_2H_5)_4$, $Ti(OC_4H_9)_4$, $Ti(OCH(CH_3)_2)_4$, and $Zn(CH_3COO)_2.2H_2O$. Of these, since it is possible to obtain the target product with good yield in the case of using a protonic acid, it is preferably used. More preferably, methanesulfonic acid by which the reaction proceeds smoothly and which is easily available is used.

The acid can be used in an amount of 0.01 to 10 moles to 1 mole of the lactone derivative (the formula (2)) as the raw material. If it is less than 0.01 moles, the reaction rate becomes too slow, and yield of the target lactone containing acrylate (the formula (4)) is very small. Thus, it is not practical. Even if the acid is added in an amount of 10 times that by mol, the yield improvement effect cannot be expected, and by-products increase, too. More preferably, the acid of 0.1 to 1.5 times that of the substrate is used, thereby achieving an appropriate reaction rate and a good yield.

The reason why base is used in the present reaction is to capture an acid (hydrogen chloride) that is generated in the reaction, in case that acid chloride is used as an acrylic acid derivative. It is possible to use organic bases such as pyridine, lutidine, triethylamine, diethylamine, piperidine, pyrrolidine, and 1,8-diazabicyclo[5,4,0]-7-undecene, as well as inorganic bases such as sodium hydroxide, sodium carbonate, sodium hydrogencarbonate, potassium hydroxide, potassium carbonate, potassium hydrogencarbonate, sodium hydride, sodium methoxide, sodium ethoxide, sodium tert-butoxide, and potassium tert-butoxide. Preferably, organic bases are used, particularly lutidine, pyridine, and triethylamine. The base is used in 1–10 moles, preferably 1–3 moles, relative to 1 mol of the compound of the formula (2).

The solvent is not particularly limited, as long as it is not involved in the reaction and as long as it dissolves the lactone derivative (the formula (2)) as the raw material. For example, it can be exemplified by hydrocarbons such as hexane, heptane, benzene, toluene and xylene; ethers such as diethyl ether, tetrahydrofuran and dioxane; halogenated hydrocarbons such as dichloromethane and chloroform; and aprotic polar solvents such as acetonitrile, N,N-dimethylformamide, dimethylsulfoxide and hexamethylphosphoric triamide. These can be used alone or in mixture of at least two.

Although the reaction temperature is not particularly limited, the reaction is generally possible in a range of −10° C. to 150° C. Since the reaction rate changes by the above-mentioned acrylic acid derivative, the type and the amount of acid and base, reaction temperature and the like, the reaction time is suitably changed in accordance with this. Actually, the reaction is conducted while the reaction solution is sequentially analyzed in the reaction, and it is possible to conduct the reaction until the raw material is consumed.

A lactone-containing acrylate derivative (the formula (4)) obtained by the above method can be isolated and purified by methods generally used for isolation and purification of organic compounds. For example, an extraction is conducted by adding an organic solvent such as ethyl acetate to the reaction mixture, and the resulting organic layer is concentrated, followed by purification such as distillation, recrystallization and column chromatography.

Next, a high molecular compound according to the present invention is explained. A high molecular compound of the present invention refers to a high molecular material prepared by homopolymerization or copolymerization of a lactone-containing monomer of the formula (3) or (4).

As a monomer that is copolymerizable with the polymerizable lactone-containing monomer of the present invention is specifically exemplified, a copolymerization with at least one monomer selected from at least acrylic esters, methacrylic esters, fluorine-containing acrylic esters, fluorine-containing methacrylic esters, styrene compounds, fluorine-containing styrene compounds, vinyl ethers, fluorine-containing vinyl ethers, allyl ethers, fluorine-containing allyl ethers, olefins, fluorine-containing olefins, norbornene compounds, and fluorine-containing norbornene compounds is preferable.

An acrylic ester or methacrylic ester usable in the present invention can be used without particular limitation with respect to ester side chain. As known compounds are exemplified, it is possible to use alkyl esters of acrylic acid or methacrylic acid such as methyl acrylate or methacrylate, ethyl acrylate or methacrylate, n-propyl acrylate or methacrylate, isopropyl acrylate or methacrylate, n-butyl acrylate or methacrylate, isobutyl acrylate or methacrylate, n-hexyl acrylate or methacrylate, n-octyl acrylate or methacrylate, 2-ethylehexyl acrylate or methacrylate, lauryl acrylate or methacrylate, 2-hydroxyethyl acrylate or methacrylate, and 2-hydroxypropyl acrylate or methacrylate; acrylates or methacrylates containing ethylene glycol, propylene glycol and tetramethylene glycol groups; unsaturated amides such as acrylamide, methacrylamide, N-methylolacrylamide, N-methylolmethacrylamide, and diacetoneacrylamide; acrylonitrile, methacrylonitrile, alkoxysilane-containing vinyl silane, acrylic or methacrylic esters, t-butyl acrylate or methacylate, 3-oxocyclohexyl acrylate or methacrylate, adamantyl acrylate or methacrylate, alkyladamantyl acrylate or methacrylate, cyclohexyl acrylate or methacrylate, tricyclodecanyl acrylate or methacrylate, an acrylate or methacrylate having a ring structure such as lactone ring and norbornene ring, acrylic acid, methacrylic acid, and the like. Furthermore, it is possible to copolymerize the above-mentioned acrylate compounds containing a cyano group at α position and their analogous compounds such as maleic acid, fumaric acid, and maleic anhydride.

Fluorine-containing acrylic esters and fluorine-containing methacrylic esters usable in the present invention are monomers containing fluorine atom or fluorine-containing group at acrylic α position or acrylic esters or methacrylic esters having a substituent containing fluorine atom at ester moiety. A fluorine-containing compound containing fluorine at α position and ester moiety is also preferable. Furthermore, a cyano group may be introduced into cyano group. For example, as a monomer in which a fluorine-containing alkyl group has been introduced into a position, there are preferably used monomers in which trifluoromethyl group, trifluoroethyl group, nonafluoro-n-butyl group, and the like are provided at a position of the above-mentioned non-fluoro acrylic ester or methacrylic ester. The ester moiety in this case is not necessarily required to contain fluorine. In case that α-trifluoromethyl acrylic alkyl ester is used as a copolymerizing component, yield of the polymer is relatively high, and dissolution of the obtained polymer in organic solvent is good. Therefore, it is preferably used.

In contrast, the monomers containing fluorine at their ester moiety are acrylates or methacrylates, having fluorine alkyl group such as perfluoroalkyl group and fluoroalkyl group, or a unit in which a cyclic structure and fluorine atom are coexistent at the ester moiety. The cyclic structure is a fluorine-containing benzene ring replaced, for example, with fluorine atom, trifluoromethyl group or hexafluorocarbinol group, fluorine-containing cyclopentane ring, fluorine-containing cyclohexane ring, fluorine-containing cycloheptane ring or the like. Furthermore, it is also possible to use an acrylate or methacrylate in which ester moiety is a fluorine-containing t-butyl ester group. It is also possible to use monomers in which these fluorine-containing functional groups are used together with fluorine-containing alkyl groups at α position. In exemplifying particularly representative ones of such units in the form of monomer, there are cited 2,2,2-trifluoroethylacrylate, 2,2,3,3-tetrafluoropropylacrylate, 1,1,1,3,3,3-hexafluoroisopropylacrylate, heptafluoroisopropylacrylate, 1,1-dihydroheptafluoro-n-butylacrylate, 1,1,5-trihydrooctafluoro-n-pentylacrylate, 1,1,2,2-tetrahydrotridecafluoro-n-octylacrylate, 1,1,2,2-tetrahydroheptadecafluoro-n-decylacrylate, 2,2,2-trifluoroethylmethacrylate, 2,2,3,3-tetrafluoropropylmethacrylate, 1,1,1,3,3,3-hexafluoroisopropylmethacrylate, heptafluoroisopropylmethacrylate, 1,1-dihydroheptafluoro-n-butylmethacrylate, 1,1,5-trihydrooctafluoro-n-pentylmethacrylate, 1,1,2,2-tetrahydrotridecafluoro-n-octylmethacrylate, 1,1,2,2-tetrahydroheptadecafluoro-n-decylmethacrylate, perfluorocyclohexylmethylacrylate, perfluorocyclohexylmethylmethacrylate, 6-[3,3,3-trifluoro-2-hydroxy-2-(trifluoromethyl)propyl]bicyclo[2.2.1]heptyl-2-ylacrylate, 6-[3,3,3-trifluoro-2-hydroxy-2-(trifluoromethyl)propyl]bicyclo[2.2.1]heptyl-2-yl 2-(trifluoromethyl)acrylate, 6-[3,3,3-trifluoro-2-hydroxy-2-(trifluoromethyl)propyl]bicyclo[2.2.1]heptyl-2-ylmethacrylate, 1,4-bis(1,1,1,3,3,3-hexafluoro-2-hydroxyisopropyl)cyclohexylacrylate, 1,4-bis(1,1,1,3,3,3-hexafluoro-2-hydroxyisopropyl)cyclohexylmethacrylate 1,4-bis(1,1,1,3,3,3-hexafluoro-2-hydroxyisopropyl)cyclohexyl 2-trifluoromethylacrylate and the like Furthermore, as styrene compounds and fluorine-containing styrene compounds usable in the present invention, it is possible to use a compound in which one or a plurality of hexafluorocarbinol groups or functional groups, in which their hydroxy group has been modified, as well as styrene, fluorinated styrene, hydroxystyrene and the like. That is, a styrene or hydroxystyrene in which fluorine atom or trifluoromethyl group has been substituted for hydrogen, the above styrene in which halogen, alkyl group or fluorine-containing alkyl group has been attached to α position, and a styrene containing perfluorovinyl group are preferably usable.

As vinyl ethers, fluorine-containing vinyl ethers, allyl ethers, and fluorine-containing allyl ethers, it is also possible to use an alkyl vinyl ether or alkyl allyl ether that optionally contains methyl group, ethyl group, propyl group, butyl group, or hydroxyl group such as hydroxyethyl group and hydroxybutyl group; a cyclic vinyl ether or allyl ether containing a cyclohexyl group or a hydrogen or carbonyl bond in its cyclic structure; and a fluorine-containing vinyl ether or fluorine-containing allyl ether containing fluorine atoms substituted for a part or all of the hydrogen of the above functional groups. They can be used without particular limitation as long as they are vinyl esters, vinyl silanes, olefins, fluorine-containing olefins, norbornene compounds, fluorine-containing norbornene compounds and other compounds containing polymerizable unsaturated bonds.

The olefins can be exemplified by ethylene, propylene, isobutene, cyclopentene, cyclohexene, and the like. The fluorine-containing olefins can be exemplified by vinyl fluoride, vinylidene fluoride, trifluoroethylene, chlorotrifluoroethylene, tetrafluoroethylene, hexafluoropropylene, hexafluoroisobutene, and the like.

The norbornene compounds and fluorine-containing norbornene compounds are norbornene monomers having a mononucleus or multinucleus structure. Upon this, the fluorine-containing olefins, allyl alcohols, fluorine-containing allyl alcohols, homoallyl alcohols and fluorine-containing homoallyl alcohols are norbornene compounds such as 3-(5-bicyclo [2.2.1]heptene-2-yl)-1,1,1-trifluoro-2-(trifluoromethyl)-2-propanol produced by a Diels-Alder addition reaction of unsaturated compounds such as acrylic acid, α-fluoroacrylic acid, α-trifluoromethylacrylic acid, methacrylic acid, and all of the acrylic esters, methacrylic esters, fluorine-containing acrylic esters or fluorine-containing methacrylic esters, 2-(benzoyloxy)pentafluoropropane, 2-(methoxyethoxymethyloxy)pentafluoropropene, 2-(tetrahydroxypyranyloxy)pentafluoropropene, 2-(benzoyloxy) trifluoroethylene, and 2-(methoxymethyloxy)trifluoroethylene, which are described in the present specification, with cyclopentadiene and cyclohexadiene. The above copolymerizing compounds may be used alone or in combination of at least two kinds.

Although the copolymerization compositional proportion of the lactone-containing monomer of the present invention is used without particular limitation, it is preferably selected between 10 and 100%. More preferably, it is 30–100%. If it is less than 30%, transparency and film forming property are not achieved sufficiently depending on the wavelength range of the applied field.

The polymerization process of a high molecular compound according to the present invention is not particularly limited as long as it is a generally used process. It is preferably radical polymerization, ionic polymerization or the like. In some cases, it is possible to use coordinated anionic polymerization, living anionic polymerization or the like. Herein, a more general radical polymerization is explained. That is, it may be conducted by either of batchwise, half continuous or continuous operation by a known polymerization method such as bulk polymerization, solution polymerization, suspension polymerization or emulsion polymerization in the presence of a radical polymerization initiator or radical initiating source.

The radical polymerization initiator is not particularly limited. As examples, azo compounds, peroxides and redox compounds are cited. In particular, preferable ones are azobisbutyronitrile, t-butylperoxypivalate, di-t-butylperoxide, i-butyrylperoxide, lauroylperoxide, succinic acid peroxide, dicinnamylperoxide, di-n-propylperoxydicarbonate, t-butylperoxyallyl monocarbonate, benzoyl peroxide, hydrogen peroxide, ammonium persulfate, and the like.

The reaction vessel for conducting the polymerization reaction is not particularly limited. It is optional to use a polymerization solvent in the polymerization reaction. The polymerization solvent is preferably one that does not interfere with the radical polymerization. Its typical ones are esters such as ethyl acetate and n-butyl acetate; ketones such as acetone and methyl isobutyl ketone; hydrocarbons such as toluene and cyclohexane; and alcohols such as methanol, isopropyl alcohol and ethylene glycol monomethyl ether. Furthermore, it is possible to use various solvents such as water, ethers, cyclic ethers, fluorohydrocarbons, and aromatics. These solvents can be used alone or in mixture of at least two kinds. Furthermore, it is also possible to use a molecular weight adjusting agent, such as mercaptan. The temperature for conducting the copolymerization reaction is suitably adjusted depending on the radical polymerization initiator or radical polymerization initiating source. It is preferably 20–200° C., particularly preferably 30–140° C.

As a process for removing organic solvent or water as the medium from a solution or dispersion of a high molecular compound according to the present invention that is obtained in this manner, any known process can be used. As its examples are cited, they are processes such as reprecipitation filtration or heating distillation under reduced pressure. As number average molecular weight of the obtained high molecular compound of the present invention, it is generally appropriately in a range of 1,000–100,000, preferably in a range of 3,000–50,000.

Next, a copolymer obtained with a compound having an acid labile group is explained. The purpose of acid labile group is to achieve positive photosensitivity and dissolution in an alkali aqueous solution after exposure to a high energy radiation such as a far infrared radiation of a wavelength of 300 nm or shorter, excimer laser, X ray or the like, or electron beam. One having fluorine atom at its functional group is for providing transparency, and one having a cyclic structure is for providing characteristics such as etching resistance and high glass transition temperature (Tg) point. They can be used differently depending on the applied fields of the present invention.

The compound having an acid labile group refers to a compound having the after-mentioned acid labile group and polymerizing group. The acid labile group refers to a group that generates elimination by the effect of photoacid generator, hydrolysis or the like. As it is exemplified, it is possible to cite alkoxycarbonyl group, acetal group, silyl group, acyl group and the like. The alkoxycarbonyl group can be exemplified by tert-butoxycarbonyl group, tert-amyloxycarbonyl group, methoxycarbonyl group, ethoxycarbonyl group, and i-propoxycarbonyl group. As the acetal group, there are cited methoxymethyl group, ethoxyethyl group, butoxyethyl group, cyclohexyloxyethyl group, benzyloxyethyl group, phenethyloxyethyl group, ethoxypropyl group, benzyloxypropyl group, phenethyloxypropyl group, ethoxybutyl group, ethoxyisobutyl group and the like. In case that $R^2$ and $R^3$ are hydrogen atoms, it is also possible to use an acetal group in which a vinyl ether has been added to the hydroxy group. As the silyl group, it is possible to cite, for example, trimethylsilyl group, ethyldimethylsilyl group, methyldiethylsilyl group, triethylsilyl group, i-propyldimethylsilyl group, methyldi-i-propylsilyl group, tri-i-propylsilyl group, t-butyldimethylsilyl group, methyldi-t-butylsilyl group, tri-t-butylsilyl group, phenyldimethylsilyl group, methyldiphenylsilyl group, triphenylsilyl group, and the like. As the acyl group, it is possible to cite acetyl group, propionyl group, butyryl group, heptanoyl group, hexanoyl group, valeryl group, pivaloyl group, isovaleryl group, lauryloyl group, myristoyl group, palmitoyl group, stearoyl group, oxalyl group, malonyl group, succinyl group, glutaryl group, adipoyl group, piperoyl group, suberoyl group, azelaoyl group, sebacoyl group, acryloyl group, propioloyl group, methacryloyl group, crotonoyl group, oleoyl group, maleoyl group, fumaroyl group, mesaconoyl group, campholoyl group, benzoyl group, phthaloyl group, isophthaloyl group, terephthaloyl group, naphthoyl group, toluoyl group, hydratoropoyl group, atoropoyl group, cinnamoyl group, furoyl group, thenoyl group, nicotinoyl group, isonicotinoyl group, and the like. Furthermore, it is also possible to use ones in which fluorine atoms have been substituted for a part or entirety of hydrogen atoms of these acid labile groups.

The polymerizing group can be exemplified by acrylic esters, methacrylic esters, fluorine-containing acrylic esters, fluorine-containing methacrylic esters, styrene compounds, fluorine-containing styrene compounds, vinyl ethers, fluorine-containing vinyl ethers, allyl ethers, fluorine-containing allyl ethers, olefins, fluorine-containing olefins, norbornene compounds, fluorine-containing norbornene compounds, and the like. The copolymers obtained with compounds having acid labile groups refer to high molecular materials obtained by copolymerizing compounds having the above acid labile groups and polymerizing groups with lactone-containing monomers represented by the formulas (3) and (4).

A high molecular compound of the present invention can be used as resist material, particularly as chemically amplified one, more particularly as a base resin of chemically amplified positive resist material. Other high molecular compounds can be mixed therewith for the purpose of changing alkali solubility and other characteristics. Upon this, although the range of high molecular compounds for mixing is not particularly limited, it can be mixed with known high molecular compounds for resist in an arbitrary range.

A resist material of the present invention can be prepared by using known components except in that a high molecular compound of the present invention is used as a base resin. In particular, the chemically amplified positive resist material contains the above high molecular compound (base resin), organic solvent, and acid generator. In this case, it is optional to further mix a basic compound and a dissolution inhibitor with these resist materials.

Organic solvent usable in the present invention may be any one as long as base resin, acid generator, other additives and the like can be dissolved therein. As such organic solvent, it is possible to use ketones such as acetone, methyl ethyl ketone, cyclohexanone, methyl isoamyl ketone and 2-heptanone; polyhydric alcohols such as ethylene glycol, ethylene glycol monoacetate, diethylene glycol, diethylene glycol monoacetate, propylene glycol, propylene glycol monoacetate, dipropylene glycol, or monomethyl ether, monoethyl ether, monopropyl ether, monobutyl ether or monophenyl ether of dipropylene glycol monoacetate and the like and their derivatives; cyclic ethers such as dioxane; esters such as methyl lactate, ethyl lactate, methyl acetate, ethyl acetate, butyl acetate, methylpyruvate, ethyl pyruvate, methyl methoxypropionate, and ethyl ethoxypropionate; aromatic solvents such as xylene and toluene; fluorine-containing solvents such as fleon, alternative fleon, perfluoro compounds, hexafluoroisopropyl alcohol and the like; and a terpene-based petroleum naphtha solvent, paraffinic solvent and the like, which are high-boiling-point, weak solvents, for the purpose of increasing coatability. Although these solvents can be used alone by one or in mixture of at least two, they are not limited to these. The amount of the above solvent in use is, to 100 parts (parts by weight, hereinafter the same) of the base resin, 300–10,000 parts, particularly preferably 500–5,000 parts.

A photoacid generator used in the resist material of the present invention is not particularly limited. An arbitrary one can be used by selecting from ones used as acid generators of chemically amplified resist. As examples of such photoacid generator, there are cited diazomethanes, glyoxime derivatives, nitrobenzyl derivatives, onium salts, halogen-containing triazine compounds, β-ketosulfonic acid derivatives, disulfone derivatives, cyano group-containing oxime-sulfonate compounds, imidoylsulfonate derivatives, and other oximsulfonate compounds. These photoacid generators may be used alone or in combination of at least two. Its content is generally selected in a range of 0.5–20 parts by weight to 100 parts by weight of the high molecular compound. If this amount is less than 0.5 parts by weight, image formation is insufficient. If it exceeds 20 parts by weight, it is difficult to form a homogeneous solution. With this, storage stability tends to lower.

A compound that is capable of suppressing the diffusion rate when an acid generated from the acid generator diffuses in a resist film is suitable as the basic compound. By mixing such basic compound, it is possible to improve resolution by suppressing the acid diffusion rate in a resist film, to suppress the sensitivity change after exposure, to make the substrate and environment dependencies less, and to improve exposure margin, pattern profile and the like.

As such basic compound, there are cited ammonia, primary, secondary and tertiary aliphatic amines, mixed amines, aromatic amines, heterocyclic amines, carboxyl group-containing, nitrogen-containing compounds, sulfonyl group-containing, nitrogen-containing compounds, hydroxy group-containing, nitrogen-containing compounds, hydroxyphenyl group-containing, nitrogen-containing compounds, alcoholic nitrogen-containing compounds, amide derivatives, imide derivatives and the like.

These basic compounds can be used alone by one or in combination of at least two. Its mixing amount is suitably 0.01–2 parts, particularly 0.01–1 part, to 100 parts of the total base resins. If the mixing amount is less than 0.01 parts, the effect as an additive may not sufficiently be obtained. If it exceeds 2 parts, resolution and sensitivity may be lowered.

Dissolution inhibitor refers to one, of which dissolution in alkali aqueous solution changes by an action of acid. That is, it is a compound having an acid labile protecting group, but can be used without particular limitation in structure. General acid labile groups refer to the above-mentioned acid labile groups and are functional groups that are severed by acid. A high molecular compound using such dissolution inhibitor is insoluble or scarcely soluble prior to an active energy ray irradiation and is hydrolyzed by an acid generated by an acid generator by the active energy ray irradiation, showing solubility in alkali aqueous solution.

As the dissolution inhibitor, there is suitable a compound of a molecular weight of 3,000 or less, of which solubility in alkali developing solution changes by an action of acid, particularly a compound of a molecular weight of 2,500 or less, in which a part or entirety of hydroxy groups of a compound containing phenol, carboxylic acid derivative, hexafluoroisopropanol has been replaced with an acid labile group. The amount of those dissolution inhibitors is 20 parts or less, preferably 15 parts or less, to 100 parts of the base resin in the resist material. If it is greater than 20 parts, the resist material lowers in heat resistance.

As a method of using the resist material of the present invention, it is possible to use a conventional resist pattern forming method of photoresist technique. That is, firstly a solution of resist material is applied to a substrate such as silicon wafer by using spinner or the like, followed by drying, thereby forming a photosensitive layer. This is irradiated with a high energy ray by an exposure device through a desired mask pattern, followed by heating. Then, this is subjected to a development treatment using a developing solution, for example, an alkali aqueous solution such as 0.1–10 wt % tetramethylammonium hydroxide aqueous solution. It is possible by this forming method to obtain a pattern conforming to the mask pattern. Furthermore, if desired, it is possible to make it contain an additive that is miscible with the resist material, various additives such as an additional resin, quencher, plasticizer, stabilizer, coloring agent, surfactant, tackifier, leveling agent, defoaming agent, compatibility enhancing agent, adhesion enhancing agent, antioxidant, and the like.

A high-energy ray used in the present invention is not particularly limited. In particular, in the case of conducting a fine processing, it is effective to use an exposure device equipped with a short-wavelength high-energy ray (e.g., KrF excimer laser, ArF excimer laser, $F_2$ excimer laser, EUV laser, or X-ray) generating source. It is effective to use an immersion exposure device that makes it possible to conduct a more efficient fine processing in numerical aperture and effective wavelength by using a medium (e.g., water and fluorine-containing solvents), into which the used high-energy ray has a less absorption, at a part of the optical path. The present resist material is also preferable in the case of use in this device.

The following nonlimitative examples are illustrative of the present invention.

EXAMPLE 1

The synthesis of a compound represented by the formula (2) was conducted by the following process.

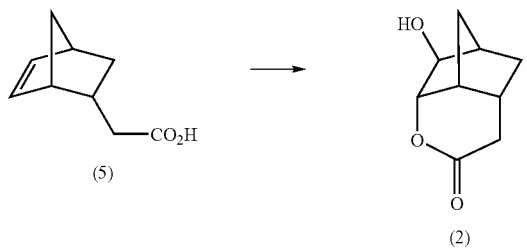

A compound (10.52 g) represented by the formula (5), water (50 g) and ammonium hydrogencarbonate (8.53 g) were sequentially added to a four-necked flask equipped with a thermometer and a rotor. The internal temperature was set to 40° C., and 30% hydrogen peroxide aqueous solution (62.01 g) was added in a dropwise manner for 30 minutes, followed by stirring for 17 hours at that temperature. Magnesium hydrogensulfite was added to the reaction liquid to treat an excess of hydrogen peroxide, followed by adding to saturated sodium bicarbonate aqueous solution to make it basic. It was extracted with ethyl acetate, followed by washing with saturated brine, then drying with anhydrous magnesium sulfate, then filtration, and then concentration of the filtrate with an evaporator. Toluene was added to the residue, followed by recrystallization to obtain a compound (6.74 g, 66%) represented by the formula (2). The identification data of the obtained compound are as follows.

$^1$H-NMR (TMS, CDCl$_3$): 0.89 (dq, 1H), 1.54(dq, 1H), 1.99 (dd, 1H), 2.05 (br, 1H), 2.11 (dq, 1H), 2.23 (m, 1H), 2.33 (m,1H), 2.41 (m,1H), 2.60(dq,2H), 3.70(d,1H), 4.55 (m,1H)

IR(cm$^{-1}$):3392, 2962, 1702, 1376, 1357, 1230, 1217, 1181, 1152, 1137, 1102, 1083, 1061, 1041, 1012, 962, 945, 807, 789, 616

GC-MS (EI method):m/e 168(M$^+$), 150(—H$_2$O), 140, 122, 111, 99, 79, 67, 55

EXAMPLE 2

The synthesis of a compound represented by the formula (6) was conducted by the following process.

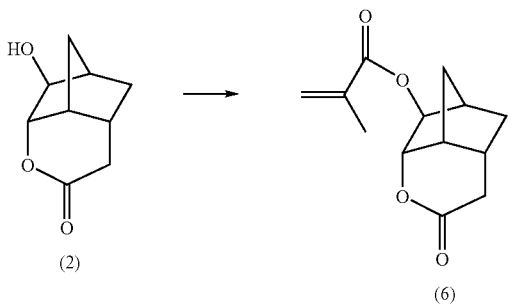

A compound (1.80 g) represented by the formula (2), toluene (18 mL), methacrylic acid anhydride (1.86 g) and methanesulfonic acid (0.10 g) were sequentially added to a four-necked flask equipped with a thermometer and a rotor, following by stirring for 6 hours at an internal temperature of 70° C. The reaction liquid was poured into saturated sodium bicarbonate aqueous solution, thereby making a two-layer separation. The organic layer was washed with saturated sodium bicarbonate aqueous solution and saturated brine, followed by drying with anhydrous magnesium sulfate, then filtration, then adding a polymerization inhibitor to the filtrate, and then concentration with an evaporator. Diisopropyl ether was added to the residue, followed by recrystallization to obtain a compound (1.52 g, 60%) represented by the formula (6). The identification data of the obtained compound are as follows.

$^1$H-NMR(TMS, CDCl$_3$): 1.07 (dq, 1H), 1.59 (dq, 1H), 1.86 (d, 1H), 1.94 (m, 3H), 2.17 (dq, 1H), 2.39(m, 1H), 2.41 (m, 1H), 2.49 (m, 1H), 2.64 (dq, 2H), 4.59 (d, 1H), 4.73 (m, 1H), 5.59 (m,1H), 6.10(m,1H)

IR(cm$^{-1}$):2959, 2869, 1730, 1716, 1635, 1376, 1355, 1324, 1309, 1226, 1176, 1153, 1121, 1061, 1041, 1006, 959, 902, 820, 804

GC-MS (EI method):m/e 236(M$^+$), 218, 208, 190, 180, 168, 150, 139, 135, 122, 109, 93, 79, 69, 55

EXAMPLE 3

A polymerization of a compound represented by the formula (6) was conducted by the following process.

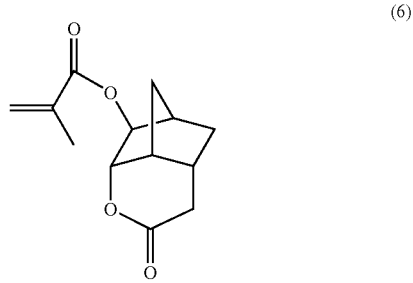

A compound (0.6 g) represented by the formula (6) was put into a flask equipped with a stirrer, and dimethyl 2,2'-azobis(2-methylpropionate) (trade name: V-601 of Wako Pure Chemical Industries, Ltd.) (4 mol %) as a polymerization initiator was added, and methyl ethyl ketone (400 wt %) as a polymerization solvent was added. This flask was heated in an oil bath of 75° C. to conduct the reaction for 16 hr. After the reaction, the reaction solution was introduced into n-hexane, followed by stirring. The resulting precipitate was filtered out, followed by vacuum drying at 50° C. for 10 hr. The composition of the obtained polymer was determined from $^1$H-NMR, and the molecular weight (Mn, Mw/Mn) was determined from GPC analysis (standard polystyrene). The results are shown in Table.

EXAMPLE 4

A copolymerization of a compound represented by the formula (6) and a compound represented by the formula (7) was conducted by the following process.

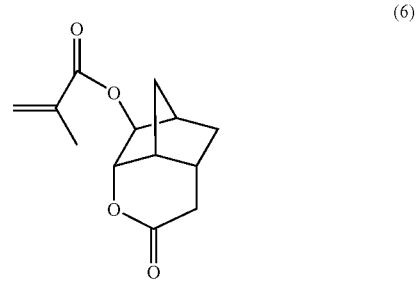

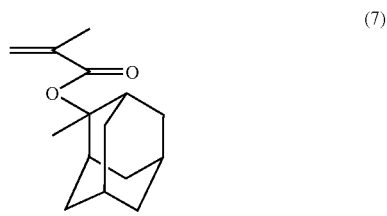

A compound (0.30 g) represented by the formula (6), a compound (0.30 g) represented by the formula (7), t-butylperoxypivalate (trade name: PERBUTYL PV of NOF CORPORATION) (4 mol %) as a polymerization initiator, and methyl ethyl ketone (400 wt %) as a polymerization solvent were sequentially put into a flask equipped with a stirrer. This flask was heated in an oil bath of 75° C. to conduct the reaction for 16 hr. After the reaction, the reaction solution was introduced into n-hexane, followed by stirring. The resulting precipitate was filtered out, followed by vacuum drying at 50° C. for 10 hr. The results are shown in Table.

EXAMPLE 5

A copolymerization of a compound represented by the formula (6), a compound represented by the formula (7) and a compound represented by the formula (8) was conducted by the following process.

(6)

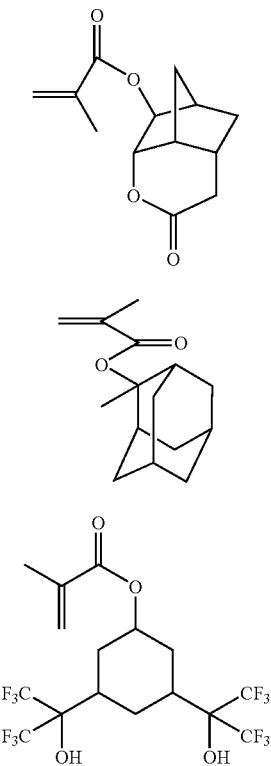

(7)

(8)

A compound (0.15 g) represented by the formula (6), a compound (0.15 g) represented by the formula (7), a compound (0.31 g) represented by the formula (8), PERBUTYL PV (4 mol %) as a polymerization initiator, and methyl ethyl ketone (400 wt %) as a polymerization solvent were sequentially put into a flask equipped with a stirrer. This flask was heated in an oil bath of 75° C. to conduct the reaction for 16 hr. After the reaction, the reaction solution was introduced into n-hexane, followed by stirring. The resulting precipitate was filtered out, followed by vacuum drying at 50° C. for 10 hr. The results are shown in Table.

EXAMPLE 6

A copolymerization of a compound represented by the formula (6), a compound represented by the formula (7) and a compound represented by the formula (9) was conducted by the following process.

(6)

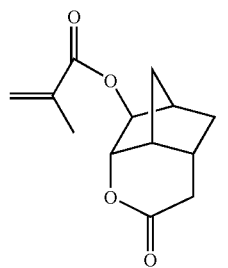

-continued (7)

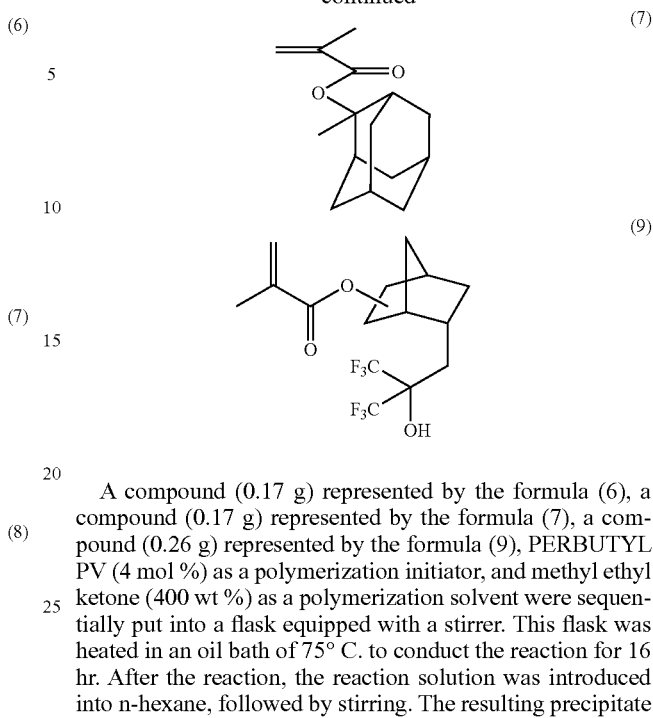

(9)

A compound (0.17 g) represented by the formula (6), a compound (0.17 g) represented by the formula (7), a compound (0.26 g) represented by the formula (9), PERBUTYL PV (4 mol %) as a polymerization initiator, and methyl ethyl ketone (400 wt %) as a polymerization solvent were sequentially put into a flask equipped with a stirrer. This flask was heated in an oil bath of 75° C. to conduct the reaction for 16 hr. After the reaction, the reaction solution was introduced into n-hexane, followed by stirring. The resulting precipitate was filtered out, followed by vacuum drying at 50° C. for 10 hr. The results are shown in Table.

EXAMPLE 7

A copolymerization of a compound represented by the formula (8), a compound represented by the formula (9), a compound represented by the formula (10) and a compound represented by the formula (11) was conducted by the following process.

(8)

(9)

(10)

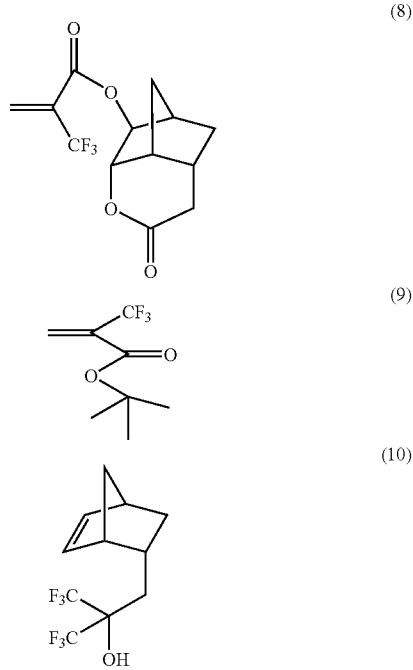

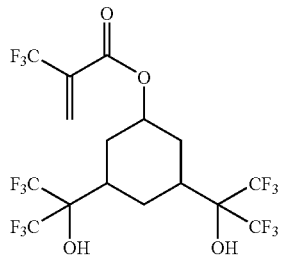

(11)

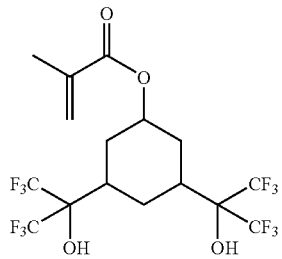

(8)

A compound (0.29 g) represented by the formula (8), a compound (0.29 g) represented by the formula (9), a compound (0.41 g) represented by the formula (10), a compound (0.56 g) represented by the formula (11), PERBUTYL PV (4 mol %) as a polymerization initiator, and methyl ethyl ketone (400 wt %) as a polymerization solvent were sequentially put into a flask equipped with a stirrer. This flask was heated in an oil bath of 75° C. to conduct the reaction for 16 hr. After the reaction, the reaction solution was introduced into n-hexane, followed by stirring. The resulting precipitate was filtered out, followed by vacuum drying at 50° C. for 10 hr. The results are shown in Table.

A compound (0.28 g) represented by the formula (12), a compound (0.30 g) represented by the formula (13), a compound (0.18 g) represented by the formula (14), a compound (0.63 g) represented by the formula (8), PERBUTYL PV (4 mol %) as a polymerization initiator, and methyl ethyl ketone (400 wt %) as a polymerization solvent were sequentially put into a flask equipped with a stirrer. This flask was heated in an oil bath of 75° C. to conduct the reaction for 16 hr. After the reaction, the reaction solution was introduced into n-hexane, followed by stirring. The resulting precipitate was filtered out, followed by vacuum drying at 50° C. for 10 hr. The results are shown in Table.

EXAMPLE 8

A copolymerization of a compound represented by the formula (12), a compound represented by the formula (13), a compound represented by the formula (14) and a compound represented by the formula (8) was conducted by the following process.

TABLE

|  | Yield | Composition | Mn | Mw/Mn |
|---|---|---|---|---|
| Example 3 | 37% |  | 4700 | 1.11 |
| Example 4 | 65% | 6/7 = 58/42 | 13300 | 2.17 |
| Example 5 | 72% | 6/7/8 = 40/29/31 | 16700 | 2.19 |
| Example 6 | 76% | 6/7/9 = 38/30/32 | 17000 | 2.22 |
| Example 7 | 62% | 8/9/10/11 = 22/31/29/19 | 12600 | 1.95 |
| Example 8 | 68% | 12/13/13/8 = 29/19/31/21 | 15400 | 2.06 |

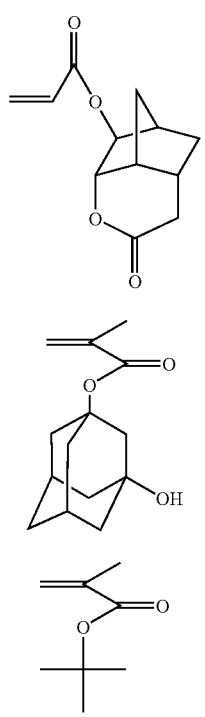

(12)

(13)

(14)

EXAMPLE 9

Resist materials were produced by the following process, and patterns were made, thereby conducting an evaluation.

The polymer obtained in Example 4–8 was dissolved in propylene glycol monomethyl ether acetate to have a solid matter concentration of 14%. Furthermore, an acid generator, triphenylsulfonium triflate made by Midori Kagaku Co., Ltd., was dissolved in an amount of 2 parts by weight per 100 parts by weight of the polymer, thereby preparing two kinds of resist solutions. These were spin coated, and light transmittances of a film thickness of 100 nm were measured at a wavelength of 193 nm. With this, they were respectively 92%, 93%, 96%, 94%, and 91% in Examples 4–8, showing high transparency in wavelengths of vacuum ultraviolet region.

Then, all of the resist solutions were filtered with 0.2 μm pore size membrane filter, followed by a spin coating of each composition solution to obtain a resist film of a film thickness of 250 nm. A preliminary baking was conducted at 110° C., followed by an exposure to 248 nm ultraviolet ray through a photomask and then a post exposure baking at 120° C. Then, a development was conducted at 23° C. for 1 minute using 2.38 wt % tetramethylammonium hydroxide aqueous solution, thereby obtaining a pattern shape that is free from resist film exfoliation and development fault.

The invention claimed is:

1. A lactone-containing monomer represented by the formula (3),

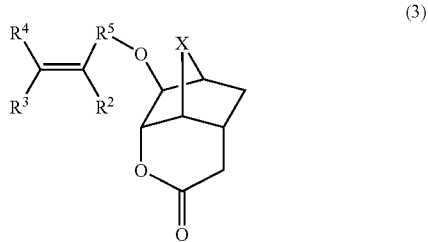

(3)

in the formula, X represents $CH_2$, $CH_2CH_2$, O, S or $NR^1$, each of $R^1$ to $R^4$ independently represents hydrogen atom, halogen atom, or a straight-chain, branched or cyclic alkyl group of carbon number of 1–10, hydrogen(s) of the alkyl group may partially or entirely be replaced with fluorine atom(s), a part of the alkyl group may contain an atomic group containing oxygen atom, sulfur atom, nitrogen atom, carbon-carbon double bond, carbonyl group, hydroxy group or carboxyl group, and $R^5$ represents a single bond, $CH_2$ or carbonyl group.

2. A lactone-containing acrylate derivative represented by the formula (4),

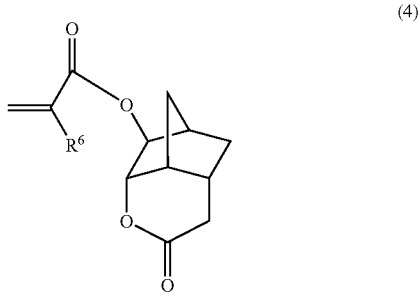

(4)

in the formula, $R^6$ represents a functional group selected from the group consisting of hydrogen atom, fluorine atom, methyl group and trifluoromethyl group.

3. A high molecular compound obtained by a polymerization or copolymerization using a compound according to claim 1.

4. A high molecular compound according to claim 3, which is obtained by copolymerizing a compound according to claim 1 with a monomer having acid lability.

5. A resist material containing a high molecular compound according to claim 3.

6. A resist material according to claim 5, further comprising a photoacid generator.

7. A pattern forming process comprising the steps of:
(a) applying a resist material according to claim 5 to a substrate to form a resist film;
(b) exposing the resist film to a high energy ray of a 1–300 nm wavelength band through a photomask;
(c) heating the exposed resist film; and
(d) developing the heated resist film with a developing solution.

8. A pattern forming process according to claim 7, wherein the high energy ray of the step (b) is KrF laser, ArF laser, $F_2$ laser, EUV laser or X-ray.

* * * * *